United States Patent [19]

Dage et al.

[11] 4,405,628

[45] Sep. 20, 1983

[54] 4-PYRIDYLIMIDAZOLONES AND METHOD OF USE

[75] Inventors: Richard C. Dage; Frank P. Palopoli; Richard A. Schnettler, all of Cincinnati, Ohio; J. Martin Grisar, Strasbourg, France

[73] Assignee: Merrell Dow Pharmaceuticals Inc., Cincinnati, Ohio

[21] Appl. No.: 314,312

[22] Filed: Oct. 23, 1981

Related U.S. Application Data

[63] Continuation-in-part of Ser. No. 240,889, Mar. 5, 1981, abandoned.

[51] Int. Cl.$^3$ .................. A61K 31/415; C07D 401/06
[52] U.S. Cl. .................. 424/263; 546/278; 548/318; 548/321; 424/273 R
[58] Field of Search ............ 546/278; 548/318, 321; 424/263, 273 R

[56] References Cited

U.S. PATENT DOCUMENTS 2,441,933  5/1948  Duschinsky .................. 548/321

FOREIGN PATENT DOCUMENTS 883856  10/1980  Belgium .................. 548/318

OTHER PUBLICATIONS

Chemical Abstracts vol. 94, Item 208864m, abstracting Belgian Pat. No. 883,856, Oct. 16, 1980 (30 pages).

*Primary Examiner*—Robert T. Bond
*Attorney, Agent, or Firm*—Stephen L. Nesbitt; Raymond A. McDonald; Gary D. Street

[57] ABSTRACT

This invention relates to aroylimidazole-2-ones and their acid and base addition salts as well as their use as cardiotonics in the treatment of cardiac failure.

20 Claims, No Drawings

4-PYRIDYLIMIDAZOLONES AND METHOD OF USE

FIELD OF THE INVENTION

This application is a continuation-in-part of copending U.S. application Ser. No. 240,889 filed Mar. 5, 1981, now abandoned.

This invention relates to aroylimidazolones and their use as cardiotonics.

SUMMARY OF THE INVENTION

This invention is directed to pharmaceutically active 1,3-dihydro-2H-imidazole-2-ones of general Formula 1

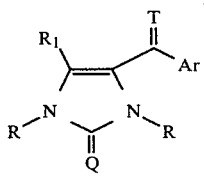

FORMULA 1 wherein Q and T are each an oxygen atom or a divalent sulfur atom; R is hydrogen, lower alkyl, lower alkanoyl, or benzoyl, $R_1$ is hydrogen or lower alkyl; Ar is pyridyl, pyrryl, thienyl, furanyl or optionally substituted phenyl and the acid base addition salts thereof with the proviso that when Q and T are both oxygen atoms then Ar cannot be thienyl, furanyl or optionally substituted phenyl. These compounds are useful as cardiotonics in the treatment of cardiac failure.

DESCRIPTION OF THE PREFERRED EMBODIMENTS

As used herein, the term "lower alkyl" includes straight or branched-chain alkyl of from 1 to 4 carbon atoms that is methyl, ethyl, propyl, isopropyl, n-butyl, isobutyl and tert-butyl.

As used herein, the term "lower alkoxy" includes straight or branched chain alkoxy of from 1 to 4 carbon atoms that is methoxy, ethoxy, n-propoxy, isopropoxy, n-butoxy, isobutoxy and tert-butoxy.

As used herein, the term "lower alkylthio" includes straight or branched chain alkylthio of from 1 to 4 carbon atoms such as methylthio, isopropylthio and n-butylthio.

As used herein, the term "halogen" includes fluorine, chlorine or bromine.

The term "lower alkanoyl" includes straight and branched chain alkanoyl groups of from 1 to 4 carbon atoms such as acetyl, propionyl, n-butyryl or isobutyryl.

As used herein, the term "optionally substituted phenyl" is taken to mean a group of the formula

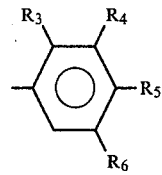

wherein $R_3$ is hydrogen, lower alkyl, lower alkoxy or lower alkylthio; $R_4$, $R_5$ and $R_6$ are each hydrogen, lower alkyl, lower alkoxy or lower alkylthio; and adjacent $R_3$, $R_4$, $R_5$ and $R_6$ groups taken together can be a methylenedioxy group optionally substituted with one or two methyl groups.

As used herein, the term "pyridyl" includes 2-,3-and 4-pyridyl. Optional substituents on the pyridyl rings of the compounds of this invention may be attached to any available carbon atom of the pyridine rings. Optional substituents on the pyridyl rings are lower alkyl, halogen, lower alkoxy or lower alkylthio groups.

As used herein, the term "furanyl" includes 2-furanyl and 3-furanyl. "Thienyl" includes 2-thienyl and 3-thienyl. "Pyrryl" includes 2-(1H-pyrryl) and 3-(1H-pyrryl).

Those compounds of Formula 1 wherein R is hydrogen are acidic and may form pharmaceutically active base addition salts of Formula 2

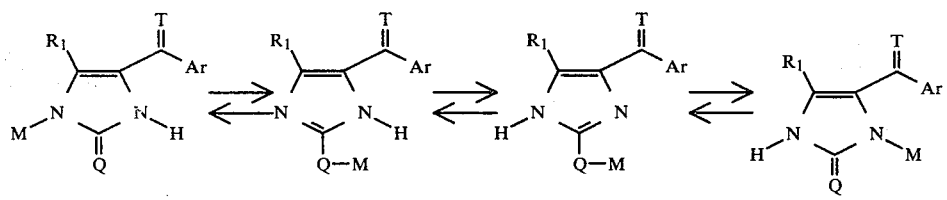

FORMULA 2 wherein Ar, Q, T and $R_1$ are defined in Formula 1, and M is a pharmaceutically acceptable alkali metal ion such as sodium or potassium ion; alkaline earth metal ion such as calcium or magnesium ion; transition metal ion such as zinc or iron ion or main group metal ion such as aluminum ion. In general, the pharmaceutically acceptable base addition salts are crystalline materials which are more soluble in water and various hydrophilic solvents and which in comparison to their free acid forms, generally demonstrate higher melting points.

The compounds of Formula 1 wherein Ar is pyridyl may form pharmaceutically active acid addition salts with both inorganic and organic acids. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic and sulfonic acids such as methane sulfonic acid and 2-hydroxyethane sulfonic acid. Such salts can exist in either a hydrated or a substantially anhydrous form. In general, the acid addition salts of these compounds are crystalline materials which are soluble in water and various hydrophilic organic solvents and which in comparison to their free base forms generally demonstrate higher melting points and an increased chemical stability.

It is apparent from the above general Formula 1 that the compounds of this invention are 1,3-dihydro-4-picolinoyl-2H-imidazole-2-ones, 1,3-dihydro-4-nicotinoyl-2H-imidazole-2-ones, 1,3-dihydro-4-isonicotinoyl-2H-imidazole-2-ones, 1,3-dihydro-4-benzoyl-2H-imidazole-2-ones, 1,3-dihydro-4-thienyloyl-2H-imidazole-2-ones, 1,3-dihydro-4-furanoyl-2H-imidazole-2-ones and 1,3-dihydro-4-pyrridyl-2H-imidazole-2-ones.

The preferred compounds of this invention are those compounds of Formula 1 wherein R is hydrogen, Q and T are each an oxygen atom and Ar is pyridyl.

The more preferred compounds of this invention are those compounds of Formula 1 wherein $R_1$ is hydrogen, methyl or ethyl.

The most preferred compounds of this invention are those compounds of Formula 1 wherein Ar is unsubstituted 4-pyridyl.

As examples of compounds of general Formula 1 there may be mentioned the following:

1,3-dihydro-4-isonicotinoyl-2H-imidazole-2-one;
4-[3-(n-butylthio)isonicotinoyl]1,3-dihydro-5-methyl-2H-imidazole-2-one;
4-(2-bromoisonicotinoyl)1,3-dihydro-5-ethyl-2H-imidazole-2-one;
4-[2-(n-butyl)isonicotinoyl]-1,3-dibenzoyl-1,3-dihydro-5-(isopropyl)-2H-imidazole-2-one, hydrochloride;
4-(n-butyl)-1,3-dihydro-5-(3-methylisonicotinoyl)-2H-imidazole-2-one;
1,3-diacetyl-1,3-dihydro-4-[2-(ethylthio)isonicotinoyl]-2H-imidazole-2-one;
1,3-dihydro-4-ethyl-5-[3-(n-propoxy)isonicotinoyl]-2H-imidazole-2-one, sodium salt;
1,3-dihydro-4-nicotinoyl-2H-imidazole-2-one;
4-(2-chloronicotinoyl)-1,3-dihydro-5-methyl-2H-imidazole-2-one;
4-(4-bromonicotinoyl)-1,3-dihydro-5-ethyl-2H-imidazole-2-ones;
4-(n-butyl)-1,3-dihydro-1,3-dimethyl-5-(5-fluoronicotinoyl)-2H-imidazole-2-one;
4-(6-chloronicotinoyl)-1,3-dihydro-5-(n-propyl)-2H-imidazole-2-one, sodium salt;
1,3-dihydro-4-ethyl-5-(2-ethylnicotinoyl)-2H-imidazole-2-one;
1,3-dihydro-4-[4-(isobutylthio)nicotinoyl]-5-(n-propyl)-2H-imidazole-2-one;
1,3-dihydro-4-isobutyl-5-(5-methylnicotinoyl)-2H-imidazole-2-one, hydrobromide;
4-(6-ethylnicotinoyl)-1,3-dihydro-2H-imidazole-2-one;
1,3-dihydro-4-ethyl-5-(2-isopropoxynicotinoyl)-2H-imidazole-2-one;
1,3-dihydro-4-(5-ethoxynicotinoyl)-5-methyl-2H-imidazole-2-one;
1,3-dihydro-4-(6-methoxynicotinoyl)-2H-imidazole-2-one;
1,3-dihydro-4-picolinoyl-2H-imidazole-2-one;
4-(3-chloropicolinoyl)-1,3-dihydro-5-ethyl-2H-imidazole-2-one;
4-(4-bromopicolinoyl)-1,3-dihydro-1,3-diethyl-5-methyl-2H-imidazole-2-one;
1,3-dihydro-4-(5-fluoropicolinoyl)-5-isopropyl-2H-imidazole-2-one;
4-(6-bromopicolinoyl)-1,3-dihydro-5-methyl-2H-imidazole-2-one;
4-[3-(n-butyl)picolinoyl]-1,3-dihydro-2H-imidazole-2-one, hydrochloride;
4-(n-butyl)-1,3-dihydro-5-[4-(methylthio)picolinoyl]-2H-imidazole-2-one;
1,3-dihydro-4-ethyl-5-(5-ethylpicolinoyl)-2H-imidazole-2-one;
1,3-dihydro-4-(6-methylpicolinoyl)-2H-imidazole-2-one;
1,3-dihydro-4-(3-ethoxypicolinoyl)-2H-imidazole-2-one;
1,3-dihydro-4-(4-isopropoxypicolinoyl)-5-ethyl-2H-imidazole-2-one;
1,3-dihydro-4-methyl-5-(5-methoxypicolinoyl)-2H-imidazole-2-one;
1,3-dihydro-4-(6-ethoxypicolinoyl)-2H-imidazole-2-one;
1,3-dihydro-4-isobutyl-5-(2-thienoyl)-2H-imidazole-2-one;
1,3-dihydro-4-ethyl-5-(3-furanoyl)-2H-imidazole-2-thione;
1,3-dihydro-4[2-(1H-pyrroyl)]-2H-imidazole-2-one;
1,3-dihydro-4-methyl-5-[4-methoxy(thiobenzoyl)]-2H-imidazole-2-thione;
4-[2-chloro(thiobenzoyl)]-1,3-dihydro-2H-imidazole-2-one;
1,3-dihydro-4-[3,4-methylenedioxy(thiobenzoyl)]-2H-imidazole-2-one; and
4-(2,3-diethylbenzoyl)-1,3-dihydro-5-ethyl-2H-imidazole-2-thione.

In general, the compounds of this invention are prepared by standard techniques analogous known in the art.

More specifically, the imidazole-2-one derivatives of Formula 1 wherein T is an oxygen atom and R is hydrogen may be prepared by reaction of an aminodiketone of Formula 3

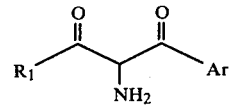

Formula 3 wherein $R_1$ and Ar are as defined in Formula 1 with a cyanate or thiocyanate salt, as appropriate, preferably sodium or potassium cyanate or thiocyanate. This reaction is performed by mixing about 1 molar equivalent of the appropriate aminodiketone with about 1 to about 5 molar equivalents, preferably about 1 molar equivalent, of a cyanate or thiocyanate salt in a suitable solvent. The reaction is allowed to proceed for about 5 minutes to about 10 hours depending on the reactants, the solvent and the temperature which can be from about 0° to about 100° C., preferably about 80° C. Suitable solvents for this reaction are any non-reactive solvents such as water or water miscible solvent, for example, an organic acid such as acetic acid; an alcohol such as methanol or ethanol; or an ether such as tetrahydrofuran or p-dioxan. Preferably any nonaqueous solvent is mixed with water. The preferred solvent is water.

The product of this reaction may be isolated by any art-known procedure such as by conversion to the corresponding sodium or potassium salt and reprecipitation with carbon dioxide or a mineral acid such as dilute hydrochloric acid.

The compounds of Formula 1 wherein Q and T are each oxygen atoms and wherein R is hydrogen may be prepared by a Friedel-Crafts acylation of a 1,3-dihydro-2H-imidazole-2-one of Formula 4

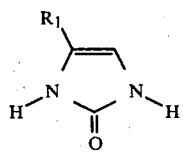

Formula 4 wherein $R_1$ is as defined in Formula 1. The acylating agent may be an optionally substituted aroyl halide, preferably an optionally substituted aroyl chloride, i.e., optionally substituted pyridoyl chlorides, benzoyl chlorides, furanoyl chlorides, thienoyl chlorides or pyrroyl chlorides.

The Friedel-Crafts reactions of this invention are performed by premixing about 1 molar equivalent of the appropriate imidazole-2-one with about 1 molar equivalent to about 10 molar equivalents, preferably about 3 to 6 molar equivalents, of a Lewis acid catalyst in a suitable solvent, for example, petroleum ethers; a chlorinated hydrocarbon, such as carbon tetrachloride, ethylene chloride, 1,1,2,2-tetrachloroethane, methylene chloride or chloroform; a chlorinated aromatic, such as 1,2,4-trichlorobenzene or o-dichlorobenzene; carbon disulfide; or nitrobenzene. The preferred solvent is 1,1,2,2-tetrachloroethane (tetrachloroethane). About 1 molar equivalent to about 10 molar equivalents, preferably about 1 molar equivalent of the appropriate aroyl compound is added, preferably dropwise, to the mixture of imidazole-2-one, Lewis acid, and solvent and the reaction is allowed to proceed for about ½ hour to about 10 hours, preferably from about 1 hour to about 5 hours depending on the reactants, the solvent, and the temperature which can be from about $-78°$ to about $150°$ C., preferably about $0°$ to about $100°$ C., most preferably about $85°$ C. The resulting aroyl imidazole-2-one may be isolated from the reaction mixture by any suitable art-known procedure, preferably by quenching the reaction mixture with ice water or water followed by neutralization with aqueous sodium bicarbonate or other weak base and subsequently removing the product by filtration or extraction with organic solvents; typically ethanol, followed by solvent removal. Purification is typically by chromatography on silica gel.

Lewis acid catalysts suitable for use in the Friedel-Crafts reactions described herein are, for example, a metal, such as aluminum, cerium, copper, iron, molybdenum, tungsten or zinc; a Bronstead acid, such as a phosphoric acid, sulfuric acid, sulfonic acid, or a hydrohalo acid, such as hydrochloric or hydrobromic acid, halogen substituted acetic acids, such as chloroacetic or trifluoroacetic acids; or a metallic halide, such as a boron halide, zinc chloride, zinc bromide, berrylium chloride, copper chloride, iron(III) bromide, iron(III) chloride, mercury(II) chloride, mercury(I) chloride, antimony bromide, antimony chloride, titanium(IV) bromide, titanium(IV) chloride, titanium(III) chloride, aluminum bromide or preferably aluminum chloride.

When it is desired that T be a divalent sulfur atom, the corresponding aroylimidazole-2-one of Formula 1 wherein T is an oxygen atom is reacted with phosphorus pentasulfide, $P_2S_5$, by procedure generally known in the art. This reaction may be performed by mixing about 1 molar equivalent of the aroylimidazole-2-one wherein T is an oxygen atom, with about 1 to about 5 molar equivalents, preferably about 1 molar equivalent, of $P_2S_5$, together with a suitable solvent. This reaction is allowed to proceed for about 1 to about 10 hours, preferably about 5 hours, depending on the reactant, the solvent and the temperature which can be from about $25°$ C. to about $125°$ C., preferably about $80°$ C. A suitable solvent for this reaction is any non-reactive solvent, for example, tetrahydrofuran, p-dioxan, benzene, toluene or pyridine. The preferred solvent is toluene.

When desired, one or both of the nitrogen atoms of the imidazole-2-one ring may be substituted with an alkyl group by any art-known procedure. Such methods include reacting the appropriate compounds of Formula 1 wherein R is hydrogen with a base and an alkylating agent in the presence of an unreactive solvent. Suitable bases for this reaction can be, for example, a hydride such as sodium hydride or calcium hydride or an alkoxide such as sodium ethoxide. Suitable alkylating agents for this reaction are, for example, an alkyl halide such as methyl iodide or a dialkylsulfate such as dimethylsulfate. Suitable unreactive solvents are, for example, dimethylformamide (DMF) or dimethylsulfoxide (DMSO). The reaction is allowed to proceed from about 1 minute to about 10 hours and the temperature may be from about $0°$ C. to about $100°$ C., preferably about $25°$ C. When it is desired that only one of the imidazole-2-one nitrogen atoms be substituted with an alkyl group, the appropriate aroylimidazole-2-one is reacted with from about 1 molar equivalent to about 10 molar equivalents of a base, preferably about 1 molar equivalent and with about 1 molar equivalent of an alkylating agent. Utilizing this procedure, both possible monoalkylating nitrogen isomers result. These isomers are separable by conventional art-known procedures such as fractional crystallization, fractional distillation or chromatography. When it is desired that both nitrogen atoms of the imidazole-2-one ring by alkyl substituted, the appropriate imidazole-2-one is reacted with from about 2 molar equivalents to about 10 molar equivalents of a base, preferably about 2 molar equivalents and from about 2 molar equivalents to about 10 molar equivalents of an alkylating agent, preferably about 2 molar equivalents.

When desired, the nitrogen atoms of the imidazole-2-one ring may be substituted with an alkanoyl or benzoyl group by any suitable art-known procedure. Such methods include reacting an imidazole-2-one of Formula 1 wherein R is hydrogen with an acyl halide, preferably an acyl chloride such as acetyl chloride, n-propanoyl chloride, isopropanoyl chloride or benzoyl chloride. Normally, acylating reactions utilizing acyl halides employ an acid sponge such as triethylamine or pyridine to remove any hydrohalide as it is formed. Furthermore, the corresponding acid anhydride may be employed instead of the acyl halides. Acylation reactions are generally run without added solvent but may be performed using any nonreactive solvent, for example, petroleum ethers; chlorinated hydrocarbons such as chloroform, methylene chloride or carbon tetrachloride; carbon disulfide; ethereal solvents, such as diethylether, tetrahydrofuran or p-dioxan or aromatic solvents such as benzene, toluene or xylene. The reactions are allowed to proceed for about 1 hour to about 20 hours, preferably about 5 hours and the temperature may be from about $0°$ to about $200°$ C., preferably about $135°$ C.

The alkali metal, alkaline earth metal, transition metal or main group metal base addition salts of the imidazole-2-ones of this invention may be prepared from a corresponding metal salt, for example, an alkoxide, such as sodium methoxide or potassium ethoxide, or a hydride such as calcium hydride. These reactions may be performed with or without a solvent. Suitable solvents are, for example, lower alcohols such as methanol, ethanol, isopropanol, n-propanol or n-butanol; or dimethylformamide (DMF). The imidazole-2-one and base are allowed to react for about 1 minute to about 24 hours, preferably about 1 hour, depending on the reactants and the temperature which can be from about −78° to about 150° C., preferably from about 0° to about 25° C.

The acid addition salts of the compounds of Formula 1 wherein Ar is pyridyl may be prepared by conventional procedures such as by treating a compound of Formula 1 with a suitable inorganic or organic acid. For example, 1-10 molar equivalents of acid is added to 1 molar equivalent of a compound of Formula 1 at a temperature of from −5° to 80° C., typically room temperature, and the reaction allowed to proceed for 0.1 to 5 hours. These reactions may be performed with or without added solvent. Suitable solvents are, for example, lower alcohols such as methanol, ethanol, isopropanol, n-propanol or n-butanol; or water.

The aminodiketones of Formula 3 may be prepared by reduction of the appropriate oxime of Formula 5

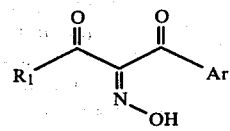

Formula 5 wherein $R_1$ and Ar are as defined above in Formula 1. These oximes are reduced by any suitable method generally known in the art such as catalytically in acidic alcoholic medium such as ethanol hydrochloric acid over an appropriate noble metal catalyst such as palladium on charcoal or with zinc or tin in acetic acid/acetic anhydride solution.

The oximes of Formula 5 may be prepared by any suitable art-known procedure such as nitrosation of the appropriate diketone of Formula 6

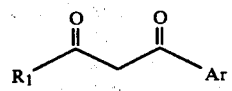

Formula 6 wherein $R_1$ and Ar are as defined above in Formula 1. Suitable nitrosation reactions are reviewed by O. Tousler in "Organic Reactions," volume VII, pp. 327–377.

The compounds of Formula 4 as well as the aroyl chlorides, i.e., pyridyl, benzoyl, pyrroyl, thienoyl and furanyl chlorides are generally known in the art or may readily be prepared by analogous techniques standard in the art.

The compounds of general Formula 1 may be used in the treatment of cardiac failure including congestive heart failure, backward heart failure, forward heart failure, left ventricular heart failure, or right ventricular heart failure or in the treatment of any other condition which requires the strengthening of heart action with a cardiotonic. In many respects these compounds possess digitalis-like action.

The utility of Formula 1 compounds as cardiotonics may be determined by administering the test compound (0.1–1.0 mg/kg) intravenously, intraperitoneally, intraduodenally or intragastrically in a suitable vehicle to a mongrel dog (either sex). The test dogs are anesthetized and prepared by isolating a suitable artery (e.g., femoral or common carotoid) and vein (e.g., femoral or external jugular); introducing polyethylene catheters filled with 0.1% Heparin-Na to record arterial blood pressure and administer compounds, respectively. The chest is opened by splitting the sternum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. Heart failure is induced by administering sodium pentobarbital (20 to 40 mg/kg) or propranalol hydrochloride (3 mg/kg) to the blood perfusing the heart. Following administration of either of these cardiac depressants, the right atrial pressure dramatically increases and cardiac output is severely depressed. Reversal of these effects by the test compound indicates cardiotonic activity.

The compounds may be administered in various manners to achieve the desired effect. The compounds may be administered alone or in the form of pharmaceutical preparations to the patient being treated either orally or parenterally, that is, intravenously or intramuscularly. The amount of compound administered will vary with the patient, the severity of the cardiac failure and the mode of administration.

For oral or parenteral administration the cardiotonically effective amount of compound is from about 0.01 mg/kg of patient body weight per day up to about 500 mg/kg of patient body weight per day and preferably from about 0.03 mg/kg of patient body weight per day up to about 200 mg/kg of patient body weight per day.

For oral administration a unit dosage may contain, for example, from 1.5 to 500 mg of the active ingredient, preferably about 10 to 100 mg of the active ingredient. For parenteral administration a unit dosage may contain, for example, from 5 to 50 mg of the active ingredient. Repetitive daily administration of the compounds may be desired and will vary with the condition of the patient and the mode of administration.

As used herein the term patient is taken to mean warm blooded animals, for example, birds, such as chickens and turkeys, and mammals, such as primates, humans, sheep, horses, bovine cows and bulls, pigs, dogs, cats, rats and mice.

For oral administration the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose and cornstarch. In another embodiment the compounds of general Formula 1 can be tableted with conventional tablet bases such as lactose, sucrose and cornstarch in combination with binders, such as acacia, cornstarch or gelatin, disintegrating agents such as potato starch or alginic acid, and a lubricant such as stearic acid or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The following are illustrative examples of the preparation and use of the compounds of this invention.

EXAMPLE 1

1,3-dihydro-4-ethyl-isonicotinoyl-2H-imidazole-2-one

To 3.0 g (27 mmole) of 1,3-dihydro-4-ethyl-2H-imidazole-2-one and 4.74 g (27 mmole) isonicotinoyl chloride hydrochloride in 100 ml tetrachloroethane is added 21.3 g (160 mmole) aluminum chloride. The mixture is stirred at 85° C. for 4 hours and quenched with water. The solution is neutralized with sodium bicarbonate and the suspension filtered. The residue is washed with ethanol and the combined filtrates evaporated to dryness. Chromatography on silica gel afforded the title compound; m.p. 260°–63°.

Following the above procedure but substituting 2-bromoisonicotinoyl chloride, 3-chloroisonicotinoyl chloride, 3-methylisonicotinoyl chloride, 2-ethoxyisonicotinoyl chloride, 3-furanoyl chloride, or 2-(1H-pyrroyl) chloride for isonicotinoyl chloride results in 4-(2-bromoisonicotinoyl)-1,3-dihydro-5-ethyl-2H-imidazole-2-one; 4-(3-chloroisonicotinoyl-1,3-dihydro-5-ethyl-2H-imidazole-2-one; 1,3-dihydro-4-ethyl-5-(3-methylisonicotinoyl)-2H-imidazole-2-one; 1,3-dihydro-4-(2-ethoxyisonicotinoyl)-5-ethyl-2H-imidazole-2-one; 1,3-dihydro-4-ethyl-5-(3-furanoyl)-2H-imidazole-2-one; or 1,3-dihydro-4-ethyl-5-[2-(1H-pyrroyl)]-2H-imidazole-2-one, respectively.

Following the procedure of Example 1 but substituting 1,3-dihydro-2H-imidazole-2-one; 1,3-dihydro-4-isobutyl-2H-imidazole-2-one or 1,3-dihydro-4-(n-propyl)-2H-imidazole-2-one for 1,3-dihydro-4-ethyl-2H-imidazole-2-one results in 1,3-dihydro-4-isonicotinoyl-2H-imidazole-2-one; 1,3-dihydro-4-isobutyl-5-isonicotinoyl-2H-imidazole-2-one; or 1,3-dihydro-4-isonicotinoyl-5-(n-propyl-2H-imidazole-2-one, respectively.

EXAMPLE 2

1,3-Dihydro-4-isonicotinoyl-5-methyl-2H-imidazole-2-one

In 80 ml tetrachloroethane are placed 3.87 g (39.5 mmole) 1,3-dihydro-4-methyl-2H-imidazole-2-one and 7 g (39.5 mmole) isonicotinoyl chloride hydrochloride. Aluminum chloride (26 g, 194 mmole) is added and the mixture is stirred at 85° C. for 3 hours. The tetrachloroethane is decanted from the reaction mixture and the residue is quenched with water and neutralized with sodium bicarbonate. The suspension is filtered and the filtrate evaporated to dryness. Chromatography over silica gel affords the title compound; m.p. 295°–96°.

Anal. calcd. for $C_{10}H_9N_3O_2$: C, 59.10; H, 4.46; N, 20.68. Found: C, 59.00; H, 4.45; N, 20.32.

EXAMPLE 3

1,3-Dihydro-4-ethyl-5-nicotinoyl-2H-imidazole-2-one

To a well stirred mixture of 8.85 g (50 mmole) nicotinoyl chloride hydrochloride and 5.6 g (50 mmole) 1,3-dihydro-4-ethyl-2H-imidazole-2-one in 100 ml tetrachloroethane is added 22 g (164 mmole) aluminum chloride. The mixture is heated at 85° C. for 2 hours and treated with water. The solution is neutralized with sodium bicarbonate, filtered and taken to dryness. Chromatography over silica gel affords the title compound; m.p. 219°–21°.

Anal. calcd. for $C_{11}H_{11}N_3O_2$: C, 60.81; H, 5.10; N, 19.34. Found: C, 60.50; H, 5.19; N, 19.47.

Using the procedure of Example 3 but substituting 2-chloronicotinoyl chloride, 4-bromonicotinoyl chloride, 5-fluoronicotinoyl chloride, 2-ethylnicotinoyl chloride, 4-isobutylnicotinoyl chloride, 5-methylnicotinoyl chloride, 6-methoxynicotinoyl chloride, picolinoyl chloride, 4-bromopicolinoyl chloride, 6-fluoropicolinoyl chloride, 3-methylpicolinoyl chloride, 5-(n-butyl)picolinoyl chloride, 4-isopropoxypicolinoyl chloride or 3-furanoyl chloride for nicotinoyl chloride results in 4-(2-chloronicotinoyl)-1,3-dihydro-5-ethyl-2H-imidazole-2-one, 4-(4-bromonicotinoyl)-1,3-dihydro-5-ethyl-2H-imidazole-2-one, 1,3-dihydro-4-ethyl-5-(5-fluoronicotinoyl)-2H-imidazole-2-one, 1,3-dihydro-4-ethyl-5-(2-ethylnicotinoyl))-2H-imidazole-2-one, 1,3-dihydro-4-ethyl-5-(4-isobutylnicotinoyl)-2H-imidazole-2-one, 1,3-dihydro-4-ethyl-5-(5-methylnicotinoyl)-2H-imidazole-2-one, 1,3-dihydro-4-ethyl-5-(6-methoxynicotinoyl)-2H-imidazole-2-one, 1,3-dihydro-4-ethyl-5-picolinoyl-2H-imidazole-2-one, 4-(4-bromopicolinoyl)-1,3-dihydro-5-ethyl-2H-imidazole-2-one, 1,3-dihydro-4-ethyl-5-(6fluoropicolinoyl)-2H-imidazole-2-one, 1,3-dihydro-4-ethyl-5-(3-methylpicolinoyl)-2H-imidazole-2-one, 4-[5-(n-butyl)-picolinoyl]-1,3-dihydro-5-ethyl-2H-imidazole-2-one, 1,3-dihydro-4-ethyl-5-(4-isopropoxypicolinoyl)-2H-imidazole-2-one; or 1,3-dihydro-4-ethyl-5-(3-furanoyl)-2H-imidazole-2-one, respectively.

EXAMPLE 4

1,3-Diacetyl-1,3-dihydro-4-ethyl-5-[2-methoxy(thiobenzoyl)]-2H-imidazole-2-one

In 100 ml Toluene are suspended 10 g of 1,3-diacetyl-1,3-dihydro-4-ethyl-5-(2-methoxybenzoyl)-2H-imidazole-2-one and 20 g phosphorus pentasulfate. The mixture is refluxed 6 hours and the solvent evaporated to yield the title compound.

Utilizing the procedure of Example 4 but substituting 1,3-dihydro-4-(4-fluorobenzoyl)-5-methyl-2H-imidazole-2-one; 1,3-dihydro-4-methyl-5-[4-(methylthio)benzoyl]-2H-imidazole-2-one; or 1,3-dihydro-4-isopropyl-5-(2-thienoyl)-2H-imidazole-2-one for 1,3-diacetyl-1,3-dihydro-4-ethyl-5-(2-methoxybenzoyl)-2H-imidazole-2-one results in 1,3-dihydro-4-[4-fluoro(thiobenzoyl)]-5-methyl-2H-imidazole-2-one; 1,3-dihydro-4-methyl-5-[4-methylthio(thiobenzoyl)]-2H-imidazole-2-one; or 1,3-dihydro-4-isopropyl-5-(thienylthiocarbonyl)-2H-imidazole-2-one, respectively.

EXAMPLE 5

1,3-Dihydro-4-methyl-5-benzoyl-2H-imidazole-2-thione

To 9.8 g 2-amino-1-phenyl-1,3-butadione in 200 ml of 1 N HCl was added 14.5 g potassium thiocyanate. The solution was warmed on the steam bath for 30 minutes and cooled. The solid title compound was recrystallized from alcohol; m.p. 268°–69°.

In a like manner, but substituting 2-amino-1-(2,3-methylenedioxyphenyl)-1,3-pentadione; 2-amino-4-methyl-1-[2-(1H-pyrryl)]-1,3-pentadione; or 2-amino-1-(4-pyridyl)-1,3-hexadione for 2-amino-1-phenyl-1-3-butadione in the above example, results in 1,3-dihydro-4-ethyl-5-(2,3-methylenedioxybenzoyl)-2H-imidazole-2-thione; 1,3-dihydro-4-isopropyl-5-[2-(1H-pyrrolyl]-2H-imidazole-2-thione; or 1,3-dihydro-4-propyl-5-isonicotinoyl-2H-imidazole-2-thione, respectively.

EXAMPLE 6

1,3-dihydro-4-(4-methoxybenzoyl)-5-methyl-2H-imidazole-2-thione

To 1.77 g 2-amino-1-(4-methoxyphenyl)-1,3-butadione in 100 ml of 1 N HCl were added 1.66 g of potassium thiocyanate. The solution was heated on the steam bath for 30 minutes and cooled. The title compound separated as a solid material, m.p. 200°.

EXAMPLE 7

1,3-Dihydro-4-ethyl-5-[3,4-difluoro(thiobenzoyl)]-2H-imidazole-2-thione

Ten grams of 1,3-dihydro-4-ethyl-5-(3,4-difluorobenzoyl)-2H-imidazole-2-thione in toluene and phosphorus pentasulfide was heated at reflux temperature for 5 hours. Evaporation of the solvent provides the title compound.

EXAMPLE 8

Cardiovascular effects of 1,3-dihydro-4-methyl-5-isonicotinoyl-2H-imidazole-2-one (RMI 19,214), 1,3-dihydro-4-ethyl-5-isonicotinoyl-2H-imidazole-2-one (RMI 19,205), and 1,3-dihydro-4-ethyl-5-nicotinoyl-2H-imidazole-2-one (RMI 19,198)

Dogs are anesthetized with sodium pentobarbital (35 mg/kg i.v.) and artificially respired. A femoral artery and vein are cannulated for measuring systemic blood pressure and injecting drugs, respectively. The chest is opened and a Walton-Brodie strain gauge arch sutured to the left ventricle to measure cardiac contractile force. Heart rate is measured from a Lead II electrocardiogram. All measurements are recorded continuously on a polygraph. RMI 19,198, RMI 19,205 and RMI 19,214 are given by intravenous injections and all increase cardiac contractile force, heart rate and decrease systemic blood pressure. Of these effects, the increase in cardiac contractile force is by far the most prominent effect of each drug. The intravenous dose of RMI 19,198, RMI 19,205 and RMI 19,214 that increases cardiac contractile force 30% is 0.16 mg/kg, 0.04 mg/kg and 0.13 mg/kg, respectively. By comparison, the doses of these compounds that increase heart rate 15% are 3.5 mg/kg, 1.5 mg/kg and 6 mg/kg, respectively. At the highest dose given, RMI 19,198 (3 mg/kg i.v.), RMI 19,205 (1 mg/kg i.v.) and RMI 19,214 (1 mg/kg i.v.) decrease systemic blood pressure only 11%, 10% and 4%, respectively.

We claim:

1. A compound of the formula

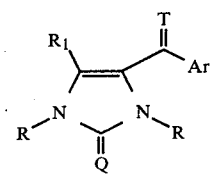

wherein Q and T are each an oxygen; R is hydrogen, lower alkyl, lower alkanoyl or benzoyl; $R_1$ is hydrogen or lower alkyl; Ar is 4-pyridyl optionally substituted with lower alkyl, halogen, lower alkoxy or lower alkylthio; and the pharmaceutically acceptable acid base addition salts thereof.

2. A compound of claim 1 wherein R is hydrogen.

3. A compound of claim 2 wherein Ar is 2- or 4-pyridyl optionally substituted with lower alkyl, halogen or lower alkoxy.

4. A compound of claim 3 wherein $R_1$ is hydrogen, methyl or ethyl.

5. A compound of claim 2 wherein Ar is 4-pyridyl optionally substituted with lower alkyl, halogen or lower alkoxy.

6. A compound of claim 5 wherein $R_1$ is hydrogen, methyl or ethyl.

7. A compound of claim 6 wherein Ar is unsubstituted 4-pyridyl.

8. A compound of claim 1 wherein Ar is unsubstituted 4-pyridyl, R is hydrogen and $R_1$ is hydrogen, that is, 1,3-dihydro-4-isonicotinoyl-2H-imidazole-2-one.

9. A compound of claim 1 wherein Ar is unsubstituted 4-pyridyl, R is hydrogen and $R_1$ is methyl, that is, 1,3-dihydro-4-isonicotinoyl-5-methyl-2H-imidazole-2-one.

10. A compound of claim 1 wherein Ar is unsubstituted 4-pyridyl, R is hydrogen and $R_1$ is ethyl, that is 1,3-dihydro-4-ethyl-5-isonicotinoyl-2H-imidazole-2-one.

11. A method of treating cardiac failure in a patient in need thereof which comprises administering to said patient a cardiotonically effective amount of a compound of the formula

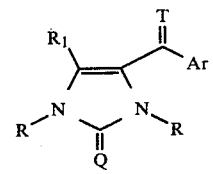

wherein Q and T are each an oxygen atom; R is hydrogen, lower alkyl, lower alkanoyl, or benzoyl; $R_1$ is hydrogen or lower alkyl; Ar is 4-pyridyl optionally substituted with lower alkyl, halogen, lower alkoxy or lower alkylthio; and the pharmaceutically acceptable acid base addition salts thereof.

12. A method of claim 11 wherein R is hydrogen.

13. A method of claim 12 wherein Ar is 2- or 4-pyridyl optionally substituted with lower alkyl, halogen or lower alkoxy.

14. A method of claim 13 wherein $R_1$ is hydrogen, methyl or ethyl.

15. A method of claim 12 wherein Ar is 4-pyridyl optionally substituted with lower alkyl, halogen or lower alkoxy.

16. A method of claim 15 wherein $R_1$ is hydrogen, methyl or ethyl.

17. A method of claim 16 wherein Ar is unsubstituted 4-pyridyl.

18. A method of claim 11 wherein Ar is unsubstituted 4-pyridyl, R is hydrogen and $R_1$ is hydrogen, that is, 1,3-dihydro-4-isonicotinoyl-2$\underline{H}$-imidazole-2-one.

19. A method of claim 11 wherein Ar is unsubstituted 4-pyridyl, R is hydrogen and $R_1$ is methyl, that is, 1,3-dihydro-4-isonicotinoyl-5-methyl-2$\underline{H}$-imidazole-2-one.

20. A method of claim 11 wherein Ar is unsubstituted 4-pyridyl, R is hydrogen and $R_1$ is ethyl, that is, 1,3-dihydro-4-ethyl-5-isonicotinoyl-2-$\underline{H}$-imidazole-2-one.

* * * * *